United States Patent [19]

Fabio et al.

[11] 4,029,788

[45] June 14, 1977

[54] 2,3-BIS(4-ALKYL-1-PIPERAZINYL)-QUINOXALINES

[75] Inventors: Paul Frank Fabio, Pearl River; Yang-I Lin, Nanuet; Stanley Albert Lang, Jr., Stony Point, all of N.Y.; Andrew Stephen Tomcufcik, Old Tappan, N.J.

[73] Assignee: American Cyanamid Company, Stamford, Conn.

[22] Filed: July 16, 1976

[21] Appl. No.: 706,027

[52] U.S. Cl. .......................... 424/250; 260/268 BC
[51] Int. Cl.² .............. A61K 31/495; C07D 295/00

[58] Field of Search ............... 260/268 BC, 250 Q; 424/250

[56] References Cited

OTHER PUBLICATIONS

Sen et al., J. Indian Chem. Soc., vol. 38 (1961), pp. 225–228.

*Primary Examiner*—Paul M. Coughlan, Jr.
*Attorney, Agent, or Firm*—Edward A. Conroy, Jr.

[57] ABSTRACT

This disclosure describes compounds of the class of 5- or 6-substituted 2,3-bis(4-alkyl-1-piperazinyl)quinoxalines useful for ameliorating cecal and hepatic amebic infestations in warm-blooded animals.

17 Claims, No Drawings

2,3-BIS(4-ALKYL-1-PIPERAZINYL)QUINOXALINES

BRIEF SUMMARY OF THE INVENTION

This invention relates to new organic compounds and, more particularly, is concerned with novel 2,3-bis(4-alkyl-1-piperazinyl)quinoxaline derivatives which may be represented by the following general formula:

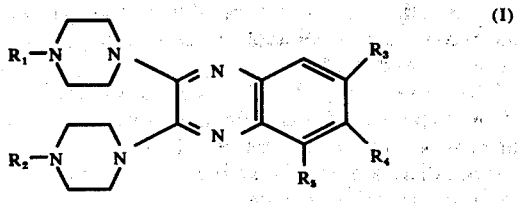

wherein $R_1$ and $R_2$ are the same and are lower alkyl, $R_3$ is hydrogen or halogen, and $R_4$ and $R_5$ are each selected from the group consisting of hydrogen, amino, p-toluenesulfonamido, p-chlorobenzenesulfonamido, p-aminobenzenesulfonamido, p-acetylaminobenzenesulfonamido, 4-(3-dimethylaminopropyl)-piperidinomethyleneamino, 2-thiophenesulfonamido, and moieties of the formulae:

$$-N=CH-O-R \text{ and } -N=\overset{R_o}{\underset{|}{C}}-N(CH_3)_2$$

wherein R is lower alkyl and $R_o$ is hydrogen or lower alkyl; with the proviso that at least one but not both of $R_4$ and $R_5$ must be hydrogen. Lower alkyl groups contemplated by the present invention are those having from 1 to 4 carbon atoms such as, for example, methyl, ethyl, isopropyl, sec-butyl, etc. whereas halogen is exemplified by chloro, bromo, and iodo.

DETAILED DESCRIPTION OF THE INVENTION

The organic bases of this invention (I) form non-toxic acid-addition and quaternary ammonium salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. Quaternary ammonium salts may be formed by reaction of the free bases with one or two equivalents of a variety of organic esters of sulfuric, hydrohalic and aromatic sulfonic acids. The organic reagents employed for quaternary ammonium salt formation are preferably lower alkyl halides. However, other organic reagents are suitable for quaternary ammonium salt formation, and may be selected from among a diverse class of compounds including benzyl chloride, phenethyl chloride, naphthylmethyl chloride, dimethyl sulfate, methyl benzenesulfonate, ethyl toluenesulfonate, allyl chloride, methallyl bromide and crotyl bromide. For purposes of this invention the free bases are equivalent to their non-toxic acid-addition and quaternary ammonium salts.

The novel compounds of the present invention are materials which may be purified by crystallization from common organic solvents such as acetone, benzene, acetonitrile, hexane, and the like. They are generally insoluble in water, but relatively soluble in organic solvents such as lower alkanols, esters, ketones, benzene, toluene, chloroform, and the like. The acid-addition and quaternary ammonium salts of the organic bases of the present invention are, in general, crystalline solids, relatively soluble in water, methanol and ethanol, but relatively insoluble in non-polar organic solvents such as ether, benzene, toluene and the like.

The intermediate 5-amino and 6-amino 2,3-bis(4-alkyl-1-piperazinyl)quinoxalines (II) may be readily prepared from the appropriately substituted 3-nitro and 4-nitro o-phenylenediamines as set forth in the following reaction scheme:

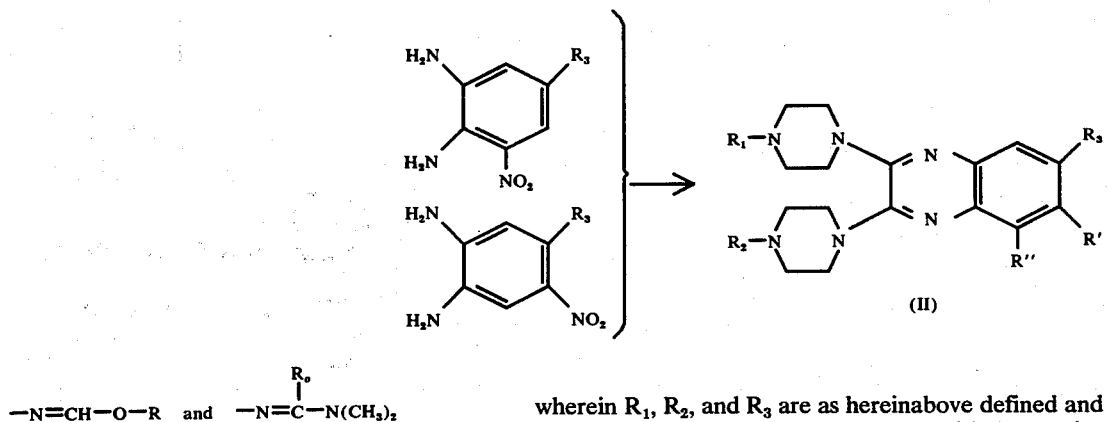

wherein $R_1$, $R_2$, and $R_3$ are as hereinabove defined and $R'$ and $R''$ are each hydrogen or amino with the proviso that at least one but not both of $R'$ and $R''$ must be hydrogen. In accordance with the above reaction scheme, a nitro-o-phenylenediamine is cyclized with oxalic acid in either 50% aqueous acetic acid or 6N hydrochloric acid at the reflux temperature for a period of time of from about one to about four hours to give the corresponding 5-nitro or 6-nitro 2,3-dihydroxyquinoxaline. This quinoxalinediol is then treated with phosphorus pentachloride at about 160°–165° C. for a few hours to provide the corresponding 5-nitro or 6-nitro 2,3-dichloroquinoxaline. Treatment of the dichloroquinoxaline with an N-alkyl-piperazine in an inert solvent such as toluene, methyl cellosolve, or xylene at a temperature of about 100°–150° C. for a period of time of a few hours to a dozen hours or more provides the corresponding 5-nitro or 6-nitro 2,3-bis(4-alkyl-1-piperazinyl)quinoxaline. Reduction of the nitro-2,3-bis(4-alkyl-1-piperazinyl)quinoxalines to the corresponding amino derivatives (II) may be achieved by either chemical or catalytic reduction using procedures well-known to those in the art. Catalytic reduction, which is especially suited for the starting nitro compounds set forth above, maybe accomplished in a solvent for the starting compound in the presence of a metal catalyst and hydrogen gas at pressures from atmospheric to superatmospheric. Ordinarily, the reduction is conveniently carried out at hydrogen pressures of from about one to about four atmospheres. Temperature does not appear to be critical in the catalytic hydrogenation. Temperatures of from 0° C. to 50° C., and usually room temperature, are preferred since they generally give best results. The metal catalyst may be of the base metal type, such as nickel or copper chromite, or it may be of the noble metal type, such as finely divided platinum, palladium or rhodium. The noble metal catalysts are advantageously employed on a carrier such as finely divided alumina, activated charcoal, diatomaceous earth, etc., in which form they are commonly available. The hydrogenation is carried out until the desired amount of hydrogen gas is absorbed at which point the hydrogenation is stopped. The solvents selected from the catalytic reduction should be reaction-inert, that is, they should not be capable of reacting with the starting materials, product, or hydrogen under the conditions of the reaction. A variety of solvents may be used for the purpose and minimum laboratory experimentation will permit the selection of a suitable solvent for any specific starting compound. Generally, the catalytic reduction may be carried out in solvents such as water, lower alkanols, e.g. methanol, ethanol; lower alkoxy loweralkanols, e.g. 2-methoxyethanol, 2-ethoxyethanol; tetrahydrofuran, dioxane, dimethylformamide, etc.

A variety of chemical reducing agents may be used in the reduction of the starting nitro compounds set forth above. These include reduction with active metals in mineral acids, e.g., zinc, tin, or iron in hydrochloric acid; reduction with metal couples such as the copper-zinc couple, the tin-mercury couple, aluminum amalgam, or magnesium amalgam; reduction with sodium sulfide in aqueous dioxane; and reduction with formic acid. Of these, reduction with sodium sulfide in aqueous dioxane at a temperature of about 90°–100° C. for a period of time of about an hour is preferred. When aqueous systems are used in the aforementioned chemical reductions, it is at times desirable to utilize a water-miscible organic solvent, particularly when the starting compound is of limited solubility in the reaction mixture. The water-miscible solvent does not alter the course of the reduction but merely provides for more efficient reduction, e.g. a shorter reaction time by providing more intimate contact of the reagents. A large number of such solvents are available for this purpose and include, among others, dimethylformamide, dimethoxyethane, methanol, ethanol, dioxane, tetrahydrofuran, and the like.

The novel N'-[2,3-bis(4-alkyl-1-piperazinyl)-5- or -6-quinoxalinyl]-N,N-dimethylamidines (III) of the present invention may be readily prepared from the intermediate aminoquinoxalines (II) as set forth in the following reaction scheme:

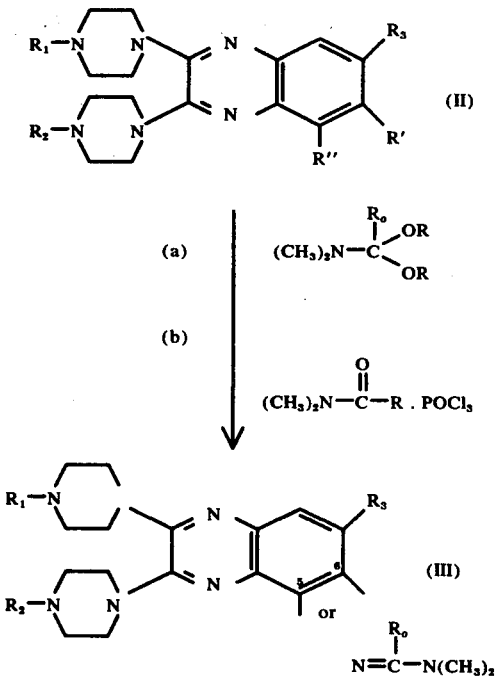

wherein $R_1$, $R_2$, $R_3$, R', R'', R and $R_o$ are as hereinbefore defined. In the acetal method, the aminoquinoxaline starting material (II) is stirred at reflux temperature with an appropriate di(lower alkyl)acetal of an N,N-dimethylamide (a) for a few hours to provide the amidine (III). In the complex method, a solution of an appropriate N,N-dimethylalkylamide and phosphorus oxychloride in acetonitrile is stirred at 0° C.–35° C. for 0.5–6 hours. The aminoquinoxaline starting material (II) is added to the solution of complex (b) and the reaction mixture is stirred at from about 25° C. to about 70° C. for one to 24 hours to provide the amidine (III).

The novel N-[2,3-bis(4-alkyl-1-piperazinyl)-5- or -6-quinoxalinyl]formimidic acid alkyl esters of the present invention may be readily prepared by refluxing a mixture of an aminoquinoxaline (II) and a tri(lower alkyl)orthoformate $HC(OR)_3$ for 12–16 hours in the presence of a catalytic amount of concentrated sulfuric acid. The novel 5- or 6-{[4-(3-dimethylaminopropyl)-piperidinomethylene]amino}-2,3-bis(4-alkyl-1- piperazinyl)quinoxalines of the present invention may be readily prepared by heating a mixture of an N-[2,3-bis-(4-alkyl-1-piperazinyl)-5- or -6-quinoxalinyl]formimidic acid alkyl ester and 4-(3-dimethylaminopropyl)piperidine at a temperature of from about 125° C. to about 175° C. for 2–5 hours. The novel N-[2,3-bis(4-alkyl-1-piperazinyl)-5- or -6-quinoxalinyl]sulfonamides of the present invention may be readily prepared by the interaction of an aminoquinoxaline (II) and a sulfonyl halide of the formula X-SO$_2$-Z wherein X is chloro or bromo and Z is p-tolyl, p-chlorophenyl, p-acetylamino-phenyl, or 2-thienyl. This reaction is carried out in a solvent inert to the reactants such as chloroform, methylene chloride, or pyridine in the presence of an acid-acceptor such as soda ash or triethylamine at ambient temperatures for 18-24 hours. The p-acetylaminophenyl products may be readily hydrolyzed to the corresponding p-aminophenyl derivatives by acidic or alkaline media as is well known to those skilled in the art.

The activity of the novel compounds of the present invention against cecal and hepatic infections in warm-blooded animals was determined by the following two tests.

Organism

The organism used in both tests was the National Institute of Health 200μ strain of *Entamoeba histolytica*. This strain and an unidentified fecal flora are cultured in Cleveland-Collier Medium at 37° C. This medium consists of a liver infusion agar base overlaid with a horse serum:saline mixture (1:6) to which is added a few milligrams of sterile rice powder. The amebas are transferred to fresh medium twice weekly.

Cecal Infections in Female Albino Wistar Rats

Pooled overlay (0.25 ml.) containing large numbers of amebas is injected into the cecums of anesthetized weanling rats during laparotomy. Treatment is begun on the day after inoculation. The test compounds are dissolved or suspended in 0.2% aqueous agar and administered once daily, by gavage, for 5 consecutive days. 6 days after inoculation of the amebas, the rats are euthanized and a scraping from the cecal wall of each rat is mixed with a drop of 0.85% saline and examined microscopically for amebas. A rat is considered cured if no amebas are seen. The cure or clearance rate (number cured/number treated) for each regimen is calculatd and corrected for non-specific cures observed in the untreated infected controls. An active dose is the lowest dose, interms of mg./kg./day, which clears or cures 50% or more of the rats so treated. The results with typical compounds of the present invention appear in Table I below together with results obtained using known effective drugs for comparison.

Hepatic Infections in Female Golden Hamsters

A piece of ameba-laden absorbable sponge, about 25 millimeters square, is inserted between the middle lobes of the livers of anesthetized hamsters during laparotomy. Untreated hamsters usually die from the resulting infection about 7 days after inoculation. Treatment is started on the day of inoculation as soon as the hamsters recover from the surgical anesthetic. The test compounds are dissolved or suspended in 0.2% aqueous agar and administered once daily, by gavage, for 5 consecutive days. Effective regimens prevent mortality. Survival rates are corrected for non-specific survival observed in untreated groups. An active dose is the lowest dose, expressed in mg./kg./day, which protects 50% or more of the hamsters so treated as evidenced by survival 14 days after inoculation. The results with typical compounds of the present invention appear in Table I below.

TABLE I

| Compound | Cecal Infection Lowest Active Dose (mg./kg./day) | Hepatic Infection Lowest Active Dose (mg./kg./day) |
| --- | --- | --- |
| N'-[2,3-bis(4-Methyl-1-piperazinyl)-6-quinozalinyl]--N,N-dimethylformamidine | 20 | 50 |
| N'-[2,3-bis(4-Methyl-1-piperazinyl)-5-quinoxalinyl]--N,N-dimethylformamidine | 10 | 50 |
| N'-[2,3-bis(4-Propyl-1-piperazinyl)-6-quinoxalinyl]-N,N-dimethylformamidine | 50 | 100 |
| 6-{[4-(3-Dimethylaminopropyl)-piperidinomethylene]-amino}-2,3-bis(4-methyl-1-piperazinyl)-quinoxaline | 50 | |
| N-[2,3-bis(4-Methyl-1-piperazinyl)-6-quinoxalinyl]--p-toluenesulfonamie | 50 | 100 |
| N'-[2,3-bis(4-Methyl-1-piperazinyl)-6-quinoxalinyl]--N,N-dimethylpropionamidine | | |
| 6-Amino-2,3-bis(4-methyl-1-piperazinyl)quinoxaline | 50 | |
| 5-Amino-2,3-bis(4-methyl-1-piperazinyl)quinoxaline | 50 | |

The novel compounds of the present invention have thus been found to be highly useful for ameliorating cecal and hepatic infections in mammals when administered in amounts ranging from about 0.5 mg. to about 100 mg. per kilogram of body weight per day. A preferred dosage regimen for optimum results would be from about two mg. to about 50 mg. per kg. of body weight per day, and such dosage units are employed that a total of from about 0.15 gram to about 3.5 grams of active ingredient for a subject of about 70 kg. body weight are administered in a 24-hour period. The compounds of the present invention may be administered by any convenient route such as orally, intraperitoneally, subcutaneously, intravenously, or intramuscularly.

Compositions according to the present invention having the desired clarity, stability, and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and the polyethylene glycols. The polyethylene glycols consist of a mixture of non-volatile, normally liquid, polyethylene glycols which are soluble in both water and organic liquids and which have molecular weights of from about 200 to about 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned nonvolatile polyethylene glycols may be employed, it is preferred to use a mixture having an average molecular weight of from about 200 to about 400.

In addition to the active compounds, the parenteral solutions of the present invention may also contain various preservatives which may be used to prevent bacterial and fungal contamination. The preservatives which may be used for such purpose are, for example, benzyl alcohol, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable anitoxidants include, for example, sodium bisulfite, sodium metabisulfite, and sodium formaldehyde sulfoxylate. Generally, from about 0.05% to about 0.2% concentrations of antioxidant are employed.

The preferred concentration of active compound is 25 to 50 mg./ml. of the finished compositions when intramuscular injection is the purpose for which the compositions are intended. They are equally adapted to intravenous administration when diluted with water or diluents employed in intravenous therapy such as isotonic glucose in appropriate quantities. For this use, initial concentrations down to about 10 to 25 mg./ml. of active compound are satisfactory. They are also adapted to oral administration when diluted with drinking water.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 200 milligrams of active compound.

The tablets, troches, pills, capsules and the like may also contain the following: a binder such as gum tragacanth, acacia, corn starch, or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

The oral liquid forms in which the novel compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like. Sterile suspensions or solutions are required for parenteral use. Isotonic preparations containing suitable preservatives are also highly desirable for parenteral use.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in this specification, these being features of the present invention.

The invention will be described in greater detail in conjunction with the following specific examples.

EXAMPLE 1

6-Amino-2,3-bis(4-methyl-1-piperazinyl)quinoxaline

A mixture of 225 g (1.47 moles) of 4-nitro-o-phenylenediamine, 375 g. (2.97 moles) of oxalic acid dihydrate and 2250 ml. of 6N hydrochloric acid is combined in a 3 necked 5 liter round bottom flask which is fitted with a reflux condenser and a teflon paddle stirrer. The suspension is heated at reflux temperature for one hour and allowed to stand at room temperature over night. The material is filtered and the dark brown solid collected is washed with five 300 ml. portions of hot distilled water. The solid is slurried in two equal portions each in 40 ml. of 2N sodium hydroxide. Each mixture is heated to near boiling with stirring and filtered hot. The red-brown hot filtrate is treated with about two liters of 4N hydrochloric acid for each batch and the slightly acidic mixtures are filtered while still hot. The brown solid collected is washed with water several times, air dried and finally dried in vacuo over phosphorous pentoxide at 78° C. to give 227.2 g of 2,3-dihydroxy-6-nitroquinoxaline. The reference for the above compound is H. I. X. Mager and W. Berends, Rec. Trav. Chim. 78, 5-21 (1959). An additional reference is F. H. S. Curd, D. G. Davey, and G. J. Stacy, Journ. Chem. Soc. 275, 1271–1277 (1949).

An 18.0 g. portion of the powdered preceding product and 42 g. of phosphorous pentachloride in a distillation apparatus is heated in an oil bath at 165° C. for two hours allowing the phosphorous oxychloride formed to distill over (8-10 ml.). Upon cooling, a molten mass is solidified which is stripped of solvent volatiles by water pump evacuation. The residue is slurried with ice and water and filtered. The solid collected is washed with water several times breaking up most of the lumps in the process and is air dried with suction. The solid is extracted three times with 100 ml. of boiling benzene and the extract is treated with activated charcoal and filtered. The filtrate is evaporated to dryness in vacuo and dried in vacuo over phosphorous pentoxide at 78° C. to give 17.6 g. of 2,3-dichloro-6-nitro-quinoxaline as a pale yellow solid.

A 9.1 g. portion of the above product is combined with a mixture of 18.7 g. of N-methylpiperazine and 150 ml. of methyl cellosolve with heat evolution. The resulting mixture is refluxed with stirring for a period of 16 hours, cooled and filtered. The solid is washed with methyl cellosolve and air dried. The solid is washed with water and air dried again followed by drying at 64° C. to give 9.5 g. of product. The filtrate above is stripped of solvent by water pump evacuation and the solid residue remaining is washed with water several times, air dried and dried at 64° C. to give 4.5 g. of product. The above solids are combined and dissolved in 150 ml. of methyl cellosolve by warming. The hot solution is filtered through paper and cooled to −10° C. The recrystallized product is collected by filtration, washed with methyl cellosolve, ethanol, and dried in vacuo over phosphorous pentoxide at 78° C. to give 10.2 g. of 2,3-bis-(4-methyl-1-piperazinyl)-6-nitroquinoxaline as a brownish yellow solid.

A 9.27 g. portion of the above product is dissolved in 100 ml. of water plus 12.5 ml. of 6N hydrochloric acid. To this solution is added 1.0 g. of 10% palladium on charcoal. Hydrogenation is conducted in a Parr shaker for 45 minutes at room temperature with an initial pressure of 50 psi. of hydrogen. During this time a total of 7.0 psi. of hydrogen is absorbed. The solution is filtered and the filtrate is allowed to stand. The addition of 10 ml. of 10N sodium hydroxide results in the formation of a precipitate which is collected by filtration. The solid is washed with water several times and air dried. Recrystallization is achieved by dissolving the solid in 300 ml. of hot acetonitrile, treating with activated charcoal, filtering through diatomaceous earth and paper, and cooling to −10° C. The recrystallized product is collected by filtration, washed several times with acetonitrile and dried in vacuo over phosphorous pentoxide at 78° C. to give 5.1 g. of 6-amino-2,3-bis(4-methyl-1-piperazinyl)quinoxaline as a yellow solid, m.p. 208°–210° C.

EXAMPLE 2

N'-[2,3-bis(4-methyl-1-piperazinyl)-6-quinoxalinyl]-N,N-dimethylformamidine

A mixture of 6.8 g. of 6-amino-2,3-bis(4-methyl-1-piperazinyl)quinoxaline (prepared as in Example 1) and 15 ml. of N,N-dimethylformamide dimethylacetal is stirred at reflux temperature for two hours. The slurry is cleared in about 20 minutes and the solution is cooled at −10° C. to form a solid mass. The solid is slurried with 15 ml. of cold diethyl ether, filtered and washed with 10 ml. of cold diethyl ether, followed by 25 ml. of petroleum ether. The material is air dried and then dried in vacuo at 60° C.

The precipitate is dissolved in 200 ml. of hot 1:1 benzene/petroleum ether and treated with activated charcoal. The clarified solution is cooled at −10° C. and the precipitate formed is collected and washed with petroleum ether. The product of the example is air dried and then dried in vacuo to yield 2.1 g., m.p. 151°–152° C.

EXAMPLE 3

5-Amino-2,3-bis(4-methyl-1-piperazinyl)quinoxaline

A mixture of 100 g. of 3-nitro-o-phenylenediamine, 160 g. of oxalic acid dihydrate and two liters of 50% aqueous acetic acid is refluxed for four hours with magnetic stirring. The reaction solution is cooled in an ice bath. The precipitate which formed was collected by filtration, washed with water and air dried followed by drying at 78° C. in vacuo to give a yellow-brown solid identified as 5-nitro-2,3-quinoxalinediol.

A 62.2 g. portion of the peceding compound (prepared as in the manner described above) is intimately mixed with 144 g. of phosphorous pentachloride in a 500 ml. reaction flask fitted with a takeoff tube with a Claisen head. The mixture is heated slowly in an oil bath. The evolution of hydrogen chloride gas is noted initially and as the temperature in the oil bath rises to 160° C. phosphorous oxychloride is distilled over. The oil bath temperature is maintained at 165°–170° C. for 90 minutes and 35 ml. of phosphorous oxychloride is collected. After a total heating time of two hours the mixture is cooled in an ice bath with formation of an oily crystallized residue which is slurried with ice plus water and filtered. The solid is washed several times with cold water, pressed dry with suction on the filter and placed in a desicator over phosphorous pentoxide overnight. The solid is extracted with three 200 ml. portions and one 100 ml. portion of chloroform. The extract is dried over anhydrous sodium sulfate and anhydrous calcium sulfate. The solvent is removed by water pump evacuation and the brown solid (48.2 g.) obtained is dried at 64° C. overnight. The insoluble solid remaining after performing the chloroform extraction above is extracted with two 100 ml. portions of acetone. The acetone extract is combined with 200 ml. of cold water. The solid precipitate is collected by filtration, pressed dry with suction on the filter and dried in vacuo over phosphorous pentoxide at 78° C. to give 7.3 g. of brown solid. The combined weight of 2,3-dichloro-5-nitro-quinoxaline obtained is 55.5 g.

A 53.8 g. portion of N-methylpiperazine is dissolved in 200 ml. of methylcellosolve and 26.1 g. of the above product is added. The mixture is refluxed for five hours with stirring and allowed to cool to room temperature overnight. The resulting mixture is stripped of solvent by water pump evacuation and the residue obtained is slurried with a small amount of ethanol. The slurry is cooled in an ice bath to −10° C. and is filtered. The solid obtained is washed two times with diethyl ether and air dried to give 33.3 g. of a yellow solid identified as 2,3-bis(4-methyl-1-piperazinyl)-5-nitro-quinoxaline.

A 33.3 g. portion of the preceding product is slurried in about 370 ml. of water plus 22.4 ml. of 12N hydrochloric acid. The suspension is divided into two portions of approximately 200 ml. each. To each portion is added 1.0 g. of 10% palladium on charcoal. Each is hydrogenated in a Parr shaker at room temperature with an initial pressure of 50 psi. of hydrogen. The time required to complete the reaction is 1½-2 hours with a hydrogen absorption of from 9.0 to 9.5 psi. Each reaction mixture is filtered through diatomaceous earth to remove the catalyst and the combined filtrate is treated with 35 ml. of 10N sodium hydroxide with separation of a gummy material. The aqueous solution is extracted with four 100 ml. portions of chloroform and the extracts are dried over anhydrous potassium carbonate and anhydrous calcium sulfate. The solvent is removed by water pump evacuation and the residue is slurried with 200 ml. of boiling ethanol and filtered hot. The solid is washed with ethanol and is air dried to give 2.4 g. of a yellow solid identified as 5-amino-2,3-bis(4-methyl-1-piperazinyl)quinoxaline, m.p. 196°–199° C.

EXAMPLE 4

N'-[2,3-bis(4-methyl-1-piperazinyl)-5-quinoxalinyl]-N,N-dimethylformamidine

A 2.4 g. portion of 5-amino-2,3-bis(4-methyl-1-piperazinyl)quinoxaline prepared as in Example 3 is combined with 23.0 1 g. of dimethylformamide diethylacetal in a reaction flask. The suspension is heated in an oil bath at 135° C. with magnetic stirring. The solid is dissolved within four minutes and refluxing is continued for 2 hours. The reaction solution is cooled and stripped of solvent by water pump evacuation. The residual yellow solid is recrystallized by boiling in 200 ml. of hexane, after filtering to remove a small amount of insoluble material. The recrystallized material is collected by filtration and dried in vacuo over phosphorous pentoxide at 78° C. The above filtrate is set aside and the dried material is again recrystallized from 200 ml. of hexane in exactly the same manner as above, collected and dried to give 0.35 g. of orange solid. A yellowish-brown insoluble material removed by filtering the hot hexane prior to cooling is set aside. The final hexane cold filtrate and the initial cold filtrate previously set aside are combined and the hexane is removed by water pump evacuation. The insoluble residue set aside previously is added to the combined filtrate residue and this is recrystallized from 70 ml. of hot acetonitrile by cooling at −10° C. The solid formed is collected by filtration, washed with cold acetonitrile and dried in vacuo over phosphorous pentoxide at 78° C. to give 1.6 g. of additional orange solid. The combined yield of the product of the example is 1.9 g., m.p. 183°–186° C.

EXAMPLE 5

6-Amino-2,3-bis(4-propyl-1-piperazinyl)quinoaxline

To a mixture of 50 g. of 1-n-propylpiperazine dihydrogen bromide and 60.0 g. of sodium bicarbonate in a reaction flask is added 200 ml. of methyl cellosolve with stirring for five minutes. To this is added 19.15 g. of 2,3-dichloro-6-nitro-quinoxaline (prepared as in Example 1) with magnetic stirring and the mixture is slowly heated to reflux. Refluxing is continued for 21 hours and the resulting mixture is cooled to 4° C. and allowed to stand. The mixture of filtered and the solid collected is washed several times with methyl cellosolve, washed several times with water and air dried to give an orange solid. This material is recrystallized from 200 ml. of benzene and 300 ml. of hexane. The precipitate is collected by filtration and is washed with hexane. The filtrate and washings are set side. The yellow solid collected is dried in vacuo over phosphorous pentoxide at 70° C. The filtrate above is then evaporated by water pump evacuation and the residue is recrystallized twice and is dried. The material obtained is combined with the yellow solid above to give 21.6 g. of 6-nitro-2,3-bis(4-propyl-1-piperazinyl)-quinoxaline.

A 16.6 g. portion of the preceding product is suspended in 150 ml. of water and plus 20 ml. of 6N hydrochloric acid. To this suspension is added 1.0 g. of 10% palladium on charcoal; then hydrogenation is conducted in a Parr shaker for one hour and 15 minutes at room temperature with an initial pressure of 50 psi. of hydrogen. During this time a total of 10.0 psi. of hydrogen is absorbed. The solution is filtered and the filtrate is allowed to stand. Upon the addition of 17 ml. of 10N sodium hydroxide a solid is formed which is collected by filtration and is washed thoroughly with water and air dried followed by drying in vacuo at 50° C. The yellow solid is dissolved in 235 ml. of hot acetonitrile, is treated with activated charcoal and is filtered through diatomaceous earth and is recrystallized by cooling at −10° C. The precipitate is collected by filtration, washed with cold acetonitrile, air dried and finally dried in vacuo at 50° C. to give 12.0 g. of a yellow solid identified as 6-amino-2,3-bis(4-propyl-1-piperazinyl)quinoxaline, m.p. 143°–146° C.

EXAMPLE 6

N'-[2,3-bis(4-propyl-1-piperazinyl)-6-quinoxalinyl]-N,N-dimethylformamidine

A 6.0 g. portion of 6-amino-2,3-bis(4-propyl-1-piperazinyl)quinoxaline (prepared as in Example 5) is mixed with 3.42 ml. of dimethylformamide dimethylacetal in a reaction flask fitted with a reflux condenser. The mixture is refluxed in an oil bath at 64° C. for three hours. The condenser is removed and the distillate is allowed to boil off as the oil bath is permitted to cool overnight. The flask is stripped of solvent by water pump evacuation and the residue is dissolved in 50 ml. of acetonitrile; is treated with activated charcoal and filtered. The filtrate is cooled at −10° C. causing separation of an oil. The supernatant is decanted and the oil is air dried to yield a crystalline solid which is recrystallized from 20 ml. of hexane by cooling at −10° C. The precipitate is filtered and is air dried to give the product of the example as a yellow solid, m.p. 95.5°–98° C.

EXAMPLE 7

N-[2,3-bis(4-methyl-1-piperazinyl)-6-quinoxalinyl]formimidic acid ethyl ester

A 17.05 g. portion of 6-amino-2,3-bis(4-methyl-1-piperazinyl)quinoxaline (prepared as in Example 1) is thoroughly mixed with 100 ml. of triethylorthoformate, then 5 drops of concentrated sulfuric acid is added with magnetic stirring and the mixture is heated at reflux in an oil bath (145°–150° C.). The solid is dissolved in about 30 minutes but shortly thereafter a yellow solid is precipitated out. Stirring is continued and the mixture allowed to reflux overnight at a distillate temperature of about 75°–80° C. After refluxing for 16 hours the reflux condenser is replaced with a takeoff condenser with a 10 cm. Vigreux column attached and 6.5 ml. of distillate with a boiling point of about 80° C. is collected over a 2½ hour period. The maximum oil bath temperature over this point of time is 180° C. The reaction mixture is cooled and the liquid layer is decanted from a small amount of insoluble material. The decanted liquid is stripped of solvent by water pump evacuation and the residual oil is triturated with 50 ml. of hexane and heated to boiling on the steam bath to dissolve the oil. The solution is cooled in an ice bath to yield a solid yellow mass. Additional hexane is added and the precipitate is filtered, washed on the filter with hexane, and pressed dry with suction to give 18.5 g. of the product of the example as a yellow solid.

EXAMPLE 8

6-{4-(3-Dimethylaminopropyl)-piperidinomethylene]amino}-2,3-bis(4-methyl-1-piperazinyl)-quinoxaline A 297 g. amount of 4-pyridine propanol (practical grade) is melted and is added portionwise to 1200 ml. of 48% hydrogen bromide solution over a 10 minute period with stirring in a 3 liter, 3 necked reaction flask. The resulting solution is refluxed for 19½ hours. The reaction mixture is cooled slightly and stripped of solvent by water pump evacuation. The solid residue is recrystallized from 1100 ml. of ethanol after treating with activated charcoal. The precipitate formed is collected by filtration, washed twice with ethanol and air dried to give 342.9 g. of pale yellow solid. The combined filtrate and washings above are reduced to about ½ volume, the solution is cooled to 4° C. and the solid formed is collected by filtration, washed with cold ethanol and air dried to give an additional 71.9 g. of pale yellow solid. The combined filtrate and washings of the above solid is combined with an equal volume of diethyl ether and cooled to 4° C. The solid formed is filtered, washed with 100 ml. of 1:1 ethanol/ether and air dried to give 84.7 g. of a tan solid. The combined weight of 499.5 g. is 4-(3-bromopropyl)-pyridine hydrobromide. The entire amount of the preceding product is added to 500 ml. of benzene and the solution is cooled to 10°–15° C. in an ice bath. A solution of 8.0 g. of sodium hydroxide in 200 ml. of cold water is carefully added to the benzene solution portionwise with stirring. The two layered liquid is then poured into a separatory funnel and an additional 50 ml. of 10N sodium hydroxide is added with thorough mixing. The aqueous layer (pH 13.0–13.5) is separated from the benzene and extracted with 200 ml. of benzene. The benzene extracts are combined and the solution is dried over anhydrous potassium carbonate and anhydrous magnesium sulfate. The dried benzene solution is placed in a 3 liter, 3 necked reaction flask fitted with a reflux condenser and a gas delivery tube with a fritted glass end extending to the bottom of the flask. The liquid is cooled to 5° C. and a total of 226 g. of dimethylamine gas is added over a 2½ hour period with stirring. Stirring is continued while the liquid is allowed to cool to room temperature overnight. A 300 ml. portion of 10N sodium hydroxide is added to the cooled reaction mixture with mixing, the layers are separated and the aqueous layer is extracted with two 250 ml. portions of benzene. The combined benzene extract is washed with three 100 ml. portions of cold water and dried over anhydrous potassium carbonate and anhydrous magnesium sulfate. The aqueous layer is saturated with potassium carbonate resulting in separation of an organic top layer which is insoluble in benzene. The organic layer is extracted twice with 250 ml. of benzene as in the saturated aqueous layer. The combination of benzene extracts is dried over anhydrous potassium carbonate and magnesium sulfate and is stripped of solvent by water pump evacuation resulting in 283.2 g. of residual oil which is distilled through a 15cm. by 2cm. Podbielniak Helipak filled column at a bath temperature ranging from 150° C. to 180° C. and controlled pressure of 9.0 to 10.0mm. The 243.1 g. fraction collected at a distillation temperature of 112°–114° C. is 4-(3-dimethylaminopropyl)pyridine.

A 16.4 g. portion of the above product is dissolved in 100 ml. of 1:1 ethyl alcohol:water plus 34.2 ml. of 5.85N hydrogen chloride in isopropyl alcohol. To this solution is added 0.5 g. of platinum oxide. The mixture is shaken in a Parr hydrogenerator at room temperature over 40 psi. of hydrogen for 3 hours and 20 minutes. Over this period of time 12 psi. of hydrogen is taken up. An additional 0.5 g. of platinum oxide is added to the mixture and the hydrogen pressure is readjusted to 40 psi. Hydrogenation is continued for 3 hours and 38 minutes with an additional uptake of 13.8 psi. of hydrogen. The reduction mixture is filtered through diatomaceous earth and the filter cake is washed with 50% aqueous ethanol. The combined filtrate and washings is stripped of solvent by water pump evacuation and the solid residue is slurried with ethanol and again stripped of solvent to dryness. The residue is readily ground to a powder in a mortar and dried in vacuo over phosphorous pentoxide at 110° C to give 4-(3-dimethylaminopropyl)piperidine dihydrochloride as an off-white solid.

A mixture of 7.75 g. of N-[2,3-bis(4-methyl-1-piperazinyl)-6-quinoxalinyl]formimidic acid ethyl ester (prepared as in Example 7) and 8.5 g. of the preceding product above is heated at reflux in an oil bath at about 140° C. for 2½ hours. The condenser is removed and the distillate is allowed to boil off. The mixture is allowed to stand at room temperature overnight. The reaction mixture is slurried with 150 ml. of boiling hexane, cooled at −10° C. and filtered. The pasty material collected is dissolved in 90 ml. of hot acetonitrile. This solution is treated with activated charcoal and filtered. The filtrate is cooled at −10° C. and the yellow solid formed is collected filtration and dried in vacuo at 78° C. over phosphorous pentoxide to give 3.9 g. of 6-{[4-(3-dimethylaminopropyl)-piperadinomethylene]amino}-2,3-bis(4-methyl-1-piperazinyl)quinoxaline, m.p. 135°–139° C.

EXAMPLE 9

N-[2,3-bis(4-methyl-1-piperazinyl)-6-quinoxalinyl]-p-toluenesulfonamide

A 6.41 g. (.020 mole) portion of 6-amino-2,3-bis-(4-methyl-1-piperazinyl)quinoxaline (prepared as in Example 1) is dissolved in 200 ml. of chloroform. Then 3.0 ml. (0.021 mole) of triethylamine is added plus 3.81 g. (0.020 mole) of p-toluenesulfonyl chloride. The resulting solution is stirred at room temperature for three hours and is left standing in a sealed flask for 18 hours. It was washed with two 50 ml. portions of distilled water and is dried over anhydrous sodium sulfate and anhydrous calcium sulfate. The solution is stripped of solvent by water pump evacuation to give a yellow solid which is dissolved in 100 ml. of hot benzene and filtered. A 200 ml. portion of cyclohexane is added to the filtrate and the resulting suspension is cooled at 4° C. and then is filtered. The collected solid is dried in vacuo at 78° C. over phosphorous pentoxide, dissolved in 475° ml. of hot acetonitrile and is filtered hot. The filtrate is cooled at −10° C. to recrystallize 3.2 g. of the final product which is collected by filtration, m.p. 234°–237° C.

EXAMPLE 10

N'-[2,3-bis(4-methyl-1-piperazinyl)-6-quinoxalinyl]-N,N-dimethylpropionamidine

To a solution of 11.33 g. (0.112 mole) of N,N-dimethylpropionamide in 110 ml. of acetonitrile (dried over molecular sieves) is added 8.3 ml. of phosphorous oxychloride at 5°–10° C. The mixture is stirred at room temperature for 90 minutes. To the resulting yellow solution is added 13.7 g. (0.040 mole) of 6-amino-2,3-bis(4-methyl-1-piperzinyl)quinoxaline (prepared as in Example 1) in several portions with stirring. The mixture is placed in an oil bath at 65° C. and stirred for 16 hours. The reaction mixture is cooled and is poured into 400 ml. of ice plus water, stirred for 10 minutes and filtered. The filtrate is made alkaline to a pH greater than 13 with 5N sodium hydroxide and extracted with five 100 ml. portions of chloroform. The combined extract is washed with two 100 ml. portions of water, dried over anhydrous potassium carbonate and anhydrous calcium sulfate and stripped of solvent by water pump evacuation to yield a residual oil which is crystallized on standing. The residue is recrystallized from 350 ml. of acetonitrile and is filtered and the solid collected is dried in vacuo at 78° C. over phosphorous pentoxide. The yellow solid obtained is dissolved in 160 ml. of hot acetonitrile, treated with activated charcoal, recrystallized by cooling at −10° C. and is filtered and dried as above to give 4.0 g. of yellow solid, m.p. 173°–175° C.

Example 11

| Preparation of capsule formulation | |
|---|---|
| Ingredient | Milligrams per capsule |
| N'-[2,3-bis(4-ethyl-1-piperazinyl)-6-quinoxalinyl]-N,N-dimethylbutyramidine | 50 |
| Starch | 80 |
| Magnesium stearate/ | 5 |

The active ingredient, starch and magnesium stearate are blended together. The mixture is used to fill hard shell capsules of a suitable size at a fill weight of 135 milligrams per capsule.

Example 12

| Preparation of tablet formulation | |
|---|---|
| Ingredient | Milligrams per tablet |
| N'-[2,3-bis(4-isopropyl-1-piperazinyl)-5-quinozalinyl]-N,N-dimethylisobutyramidine | 100 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a rate of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 100 milligrams of active ingredient.

Example 13

| Preparation of oral syrup formulation | |
|---|---|
| Ingredient | Amount |
| N'-[2,3-bis(4-ethyl-1-piperazinyl)-6-quinozalinyl]formimidic acid methyl ester | 5000 |
| Sorbitol solution (70% N.F.) | ml 40 |
| Sodium benzoate | mg 150 |
| Sucaryl | mg 90 |
| Saccharin | mg 100 |
| Red Dye (F.D. & C. No. 2) | mg 10 |
| Cherry flavor | mg 50 |
| Distilled water, qs to | ml 100 |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

Example 14

| Preparation of intramuscular formulation | |
|---|---|
| Ingredient | Amount, percent |
| N-[2,3-bis(4-methyl-1-piperazinyl)-5-quinoxalinyl]-p-aminobenzenesulfonamide dihydrochloride | 2.5 |
| Parabens (4:1 mixture of methyl and propyl) | 0.1 |
| Water for injection | 100 |

The parabens are dissolved in about one-half the volume of water for injection at 80° C. with stirring. The solution is cooled to below 40° C. and the active ingredient is dissolved therein. The cooled solution is adjusted to final volume with water for injection and is then sterilized by sterile filtration through a suitable filter.

We claim:
1. A compound selected from the group consisting of those of the formula:

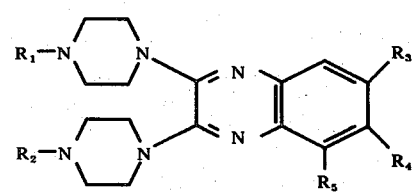

wherein $R_1$ and $R_2$ are the same and are lower alkyl; $R_3$ is hydrogen or halogen; and $R_4$ and $R_5$ are each individually selected from the group consisting of hydrogen, amino-p-toluenesulfonamido, 4-(3-dimethylaminopropyl)piperidinomethyleneamino, and moieties of the formulae:

$$-N=CH-O-R \quad \text{and} \quad -N=\overset{R_0}{\underset{|}{C}}-N(CH_3)_2$$

wherein R is lower alkyl and $R_0$ is hydrogen or lower alkyl, with the proviso that at least one but not both of $R_4$ and $R_5$ must be hydrogen; and the pharmacologically acceptable acid-addition and quanternary ammonium salts thereof.

2. The compound according to claim 1, wherein $R_1$ and $R_2$ are methyl, $R_3$ and $R_4$ are hydrogen, and $R_5$ is amino; 5-amino-2,3-bis(4-methyl-1-piperazinyl)-quinoxaline.

3. The compound according to claim 1 wherein $R_1$ and $R_2$ are methyl, $R_3$ and $R_5$ are hydrogen, and $R_4$ is amino; 6-amino-2,3-bis(4-methyl-1-piperazinyl)-quinoxaline.

4. The compound according to claim 1 wherein $R_1$ and $R_2$ are methyl, $R_3$ and $R_5$ are hydrogen, and $R_4$ is $-N=CH-N(CH_3)_2$; N'-[2,3-bis(4-methyl-1-piperazinyl)-6-quinoxalinyl]-N,N-dimethylformamidine.

5. The compound according to claim 1 wherein $R_1$ and $R_2$ are methyl, $R_3$ and $R_4$ are hydrogen, and $R_5$ is $-N=CH-N(CH_3)_2$; N'-[2,3-bis(4-methyl-1-piperazinyl)-5-quinoxalinyl]-N,N-dimethylformamidine.

6. The compound according to claim 1 wherein $R_1$ and $R_2$ are n-propyl, $R_3$ and $R_5$ are hydrogen, and $R_4$ is $-N=CH-N(CH_3)_2$; N'-[2,3-bis(4-n-propyl-1-piperazinyl)-6-quinoxalinyl]-N,N-dimethylformamidine.

7. The compound according to claim 1 wherein $R_1$ and $R_2$ are methyl, $R_3$ and $R_5$ are hydrogen, and $R_4$ is 4-(3-dimethylaminopropyl)piperidonomethyleneamino; 6-{[4-(3-dimethylaminopropyl)-piperidinomethylene]amino}-2,3-bis(4-methyl-1-piperazinyl)quinoxaline.

8. The compound according to claim 1 wherein $R_1$ and $R_2$ are methyl, $R_3$ and $R_5$ are hydrogen, and $R_4$ is p-toluene-sulfonamido; N-[2,3-bis(4-methyl-1-piperazinyl)-6-quinoxalinyl]-p-toluenesulfonamide.

9. The compound according to claim 1 wherein $R_1$ and $R_2$ are methyl, $R_3$ and $R_5$ are hydrogen, and $R_4$ is $$-N=\overset{C_2H_5}{\underset{|}{C}}-N(CH_3)_2;$$

N'-[2,3-bis(4-methyl-1-piperazinyl)-6-quinoxalinyl]-N,N-dimethylpropionamidine.

10. A method of treating a mammal to eliminate cecal and hepatic amebae therefrom which comprises administering to said mammal an effective amount of a compound selected from the group consisting of those of the formula:

wherein $R_1$ and $R_2$ are the same and are lower alkyl; $R_3$ is hydrogen or halogen; and $R_4$ and $R_5$ are each individually selected from the group consisting of hydrogen, amino, p-toluenesulfonamido, 4-(3-dimethylaminopropyl)piperidinomethyleneamino, and moieties of the formulae:

$$-N=CH-O-R \quad \text{and} \quad -N=\overset{R_0}{\underset{|}{C}}-N(CH_3)_2$$

wherein R is lower alkyl and $R_0$ is hydrogen or lower alkyl, with the proviso that at least one but not both of $R_4$ and $R_5$ must be hydrogen; and the pharmacologically acceptable acid-addition and quaternary ammonium salts thereof.

11. The method according to claim 10 wherein the compound is 6-amino-2,3-bis(4-methyl-1-piperazinyl)-quinoxaline.

12. The method according to claim 10 wherein the compound is 5-amino-2,3-bis(4-methyl-1-piperazinyl)-quinoxaline.

13. The method according to claim 10 wherein the compound is N'-[2,3-bis(4-methyl-1-piperazinyl)-6-quinoxalinyl]-N,N-dimethylformamidine.

14. The method according to claim 10 wherein the compound is N'-[2,3-bis(4-methyl-1-piperazinyl)-5-quinoxalinyl]-N,N-dimethylformamidine.

15. The method according to claim 10 wherein the compound is N'-[2,3-bis(4-propyl-1-piperazinyl)-6-quinoxalinyl]-N,N-dimethylformamidine.

16. The method according to claim 10 wherein the compound is 6-{(4-(3-dimethylaminopropyl)-piperidinomethylene]-amino}-2,3-bis(4-methyl-1-piperazinyl)quinoxaline.

17. The method according to claim 10 wherein the compound is N-[2,3-bis(4-methyl-1-piperazinyl)-6-quinoxalinyl]-p-toluenesulfonamide.

* * * * *